United States Patent [19]
Tuneberg

[11] Patent Number: 5,108,285
[45] Date of Patent: Apr. 28, 1992

[54] BONDING BASE AND METHOD OF MAKING SAME FOR A CERAMIC ORTHODONTIC BRACKET

[75] Inventor: Lee H. Tuneberg, Sheboygan, Wis.
[73] Assignee: American Orthodontics Corporation, Sheboygan, Wis.
[21] Appl. No.: 769,099
[22] Filed: Sep. 30, 1991
[51] Int. Cl.$^5$ ................................................ A61C 3/00
[52] U.S. Cl. ......................................................... 433/9
[58] Field of Search ......................... 433/8, 9; 427/379

[56] References Cited

U.S. PATENT DOCUMENTS

| | | | |
|---|---|---|---|
| 4,460,336 | 7/1984 | Smith et al. | 433/9 |
| 4,752,221 | 6/1988 | Idanson et al. | 433/9 |
| 4,838,786 | 6/1989 | Reher et al. | 433/9 |
| 4,948,366 | 8/1990 | Horn et al. | 433/9 |

OTHER PUBLICATIONS

Ormco Corporation, "Gem Brackets", 1987.
Unitex Corporation, "Transcend Series 2000", 1990.

Primary Examiner—Cary E. O'Connor
Attorney, Agent, or Firm—Lloyd L. Zickert

[57] ABSTRACT

A bonding base and method of making a base for a ceramic orthodontic bracket to provide mechanical retention between the bracket and the tooth so that the bracket may be debonded by the failure of the mechanical bond at the bracket/bond interface when the shear strength of the bond is exceeded. The bracket bonding base includes a glass frit fired to the tooth-attaching side of the bracket and a layer of textured aluminum oxide fired to the frit. The method of making the bonding base includes controlled preparation of a glass ceramic glaze (frit) to have a coefficient of thermal expansion slightly less than that of the bracket and application of the glaze to the bracket base. Thereafter, a proper firing sequence transforms the glaze into a sintered glass ceramic. A specially prepared textured substance is then applied to the sintered ceramic glaze and the bracket is again fired under controlled conditions in order to fuse the textured substance with the glaze.

16 Claims, 1 Drawing Sheet

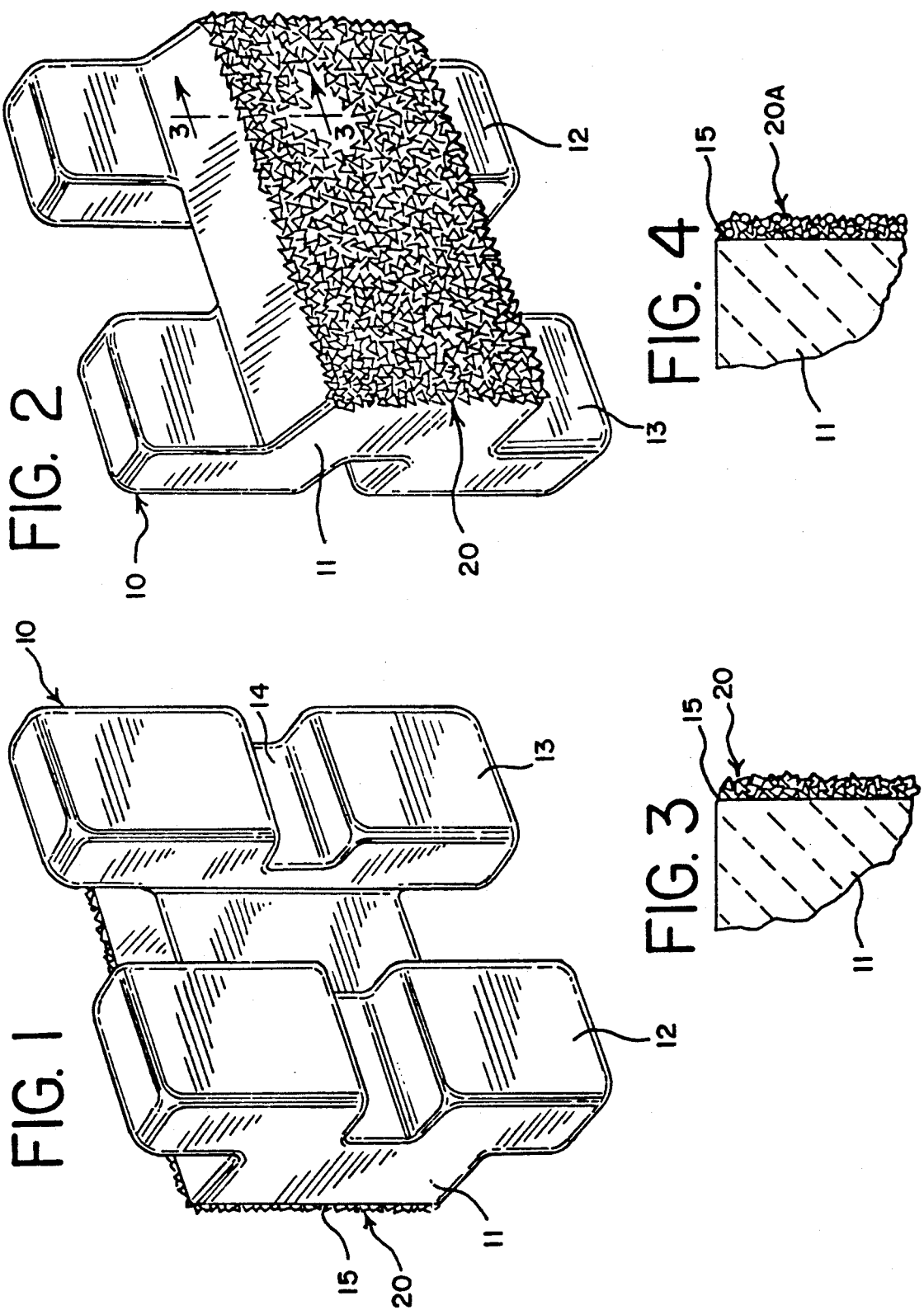

BONDING BASE AND METHOD OF MAKING SAME FOR A CERAMIC ORTHODONTIC BRACKET

DESCRIPTION

This invention relates in general to a bonding base and method for making same for a ceramic orthodontic bracket, and more particularly to a bonding base for allowing mechanical retention of the bracket to a tooth so that it may be thereafter removed from the tooth by causing failure of the mechanical bond.

BACKGROUND OF THE INVENTION

Heretofore, it has been well known to bond ceramic orthodontic brackets to teeth by use of a chemical bonding material which causes a chemical bonding between the bracket base and the tooth that results in a substantially higher bond strength than that obtained by mechanical retention in the bonding of a metal bracket to a tooth surface. Because of the higher bonding strength obtained with a chemical bond, a much higher shear force is necessary in order to debond the bracket from a tooth which has led to a number of problems during debonding. For example, the ceramic bracket being very brittle can fracture, allowing particles to be ingested by the patient. Because the bonding strength is so high, it sometimes results in causing fracture of the tooth or the removal of enamel from the tooth surface which damages the tooth.

In order to overcome the problems of bracket piece ingestion or damaging the teeth during debonding of ceramic brackets that are chemically bonded to teeth, it is known to apply a surface to the tooth-attaching side of a ceramic bracket that will provide a mechanical interlock between the bracket and the tooth as set forth in U.S. Pat. No. 4,838,786 by applying an alumina particle texturing through a combined brazing/sintering operation.

It has also been known to provide a ceramic bracket base with a microcrystalline bonding surface for obtaining a bracket that may be mechanically bonded to a tooth.

SUMMARY OF THE INVENTION

A bonding base and method of making same for a ceramic orthodontic bracket according to the present invention is an improvement over the prior known bases used for mechanical retention of brackets. The bonding base provides a bond strength similar to that accomplished with stainless steel brackets having foil mesh. Also, the ease of removal is the same as with a stainless steel bracket having foil mesh and being bonded with the standard composite resin.

The present invention is in a glass ceramic base and method for making same to be applied to a ceramic bracket such as one made of polycrystalline alumina or monocrystalline alumina, where the glass ceramic base includes alumina grit for mechanical retention of a dental bonding composite. The base is made by applying a glass ceramic glaze (frit) to the tooth-attaching side of the ceramic bracket. The glaze is suitably applied to the tooth-attaching side of the bracket base and then fired into a sintered glass ceramic. The coefficient of thermal expansion of the glass ceramic glaze is closely matched to that of the bracket to be slightly below the coefficient of thermal expansion of the bracket. A water-soluble contact adhesive is then applied to the fired glaze surface, and a textured substance or material is applied to the adhesive comprised of multi-directional undercuts and projections. The textured substance may be of sharp multi-edged shards of alpha alumina of a preferred size or small glass spheres or beads combined with the shards. Following the application of the texturing material, the entire bracket is then refired to allow the alumina shards or alumina shards/glass spheres to settle into the molten glaze. Thereafter, the bracket and base is cooled at a controlled rate.

It is therefore an object of the present invention to provide a bonding base and a method of making same for a ceramic orthodontic bracket so as to enable a mechanical retention by use of a standard bonding material, thereby eliminating the need for chemical bonding and avoiding the hazards of debonding chemically bonded brackets.

A further object of the invention is in the provision of a retention base and method of making same for a ceramic orthodontic bracket that includes the firing of a glass ceramic glaze on the tooth-attaching side of the bracket and the further application of a textured material to create a complex surface on the glaze comprised of multi-directional undercuts and projections and refiring of the bracket to fuse the textured material to the glaze.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a front perspective view of a ceramic bracket having the bonding base according to the present invention;

FIG. 2 is a perspective view of the tooth-attaching side of the bracket of FIG. 1 and showing the mechanical bonding retention base;

FIG. 3 is a somewhat schematic but greatly enlarged sectional view taken through the retention base of the bracket in FIG. 2 and generally along the lines 2—2; and FIG. 4 is a view similar to FIG. 3 but showing a modified retention base structure.

DESCRIPTION OF THE INVENTION

The bonding base of the invention is especially suitable for ceramic orthodontic brackets of the polycrystalline alumina or the monocrystalline alumina type to provide a mechanical retention base for bonding the bracket to a tooth surface with the well known and tested and proved mechanical bonding materials or adhesives long used for bonding metal brackets to teeth. Thus, the bonding base of the present invention will produce a bond strength for a bracket substantially similar to stainless steel brackets having foil mesh bases wherein debonding may be accomplished with the same ease as debonding of metal brackets with foil mesh. Thus, the heretofore well known problems of debonding ceramic brackets that are chemically bonded to teeth are obviated.

The method of making the mechanical retention base for a ceramic bracket according to the invention includes the application of a suitable glass ceramic glaze or frit, firing the glaze, applying a textured material to the glaze, refiring the bracket, and then cooling.

The glaze must be closely matched to have a coefficient of thermal expansion slightly below the coefficient of thermal expansion of the bracket. The bracket, or at least the bracket base on which the mechanical retention or bonding base is applied, is a highly purified aluminum oxide having a coefficient of thermal expansion approximately equal to $6.7$ times $10^{-6}$.

The glaze of the present invention is an alkali calcium aluminosilicate composition having a coefficient of thermal expansion approximately equal to $6.1$ times $10^{-6}$. The glaze is in the form of a dry glass ceramic blend mixed into a liquid comprised of various binders and solvents including carbowax, methylcellulose, methanol, and de-ionized water.

The dry glass ceramic blend for the glaze may include the following:

| | |
|---|---|
| $SiO_2$ | 60-70% |
| $Al_2O_3$ | 5-13% |
| Ca | 8-13% |
| Na | 10-17% |
| K | 1-5% |

An ideal glass ceramic blend composition would be the following:

| | |
|---|---|
| $SiO_2$ | 65% |
| $Al_2O_3$ | 9% |
| Ca | 10% |
| Na | 14% |
| K | 2% |

Application of the glaze to the tooth-attaching side of the bracket base may be accomplished by various methods, including dipping the bracket into the glaze, brushing the glaze onto the base of the bracket, spraying the glaze onto the base of the bracket, or by use of extruded tape. Following a closely controlled application of the glaze to the bracket, the bracket and glaze must then be subjected to a proper firing sequence to transform the glaze into a sintered glass ceramic. The materials within the glaze will be thermally fused and chemically bonded into a glass structure that does not leech constituent elements out.

The firing sequence should be ramped so that the binders and solvents are burned off early in the cycle allowing the glass to go through several stages of transformation including annealing, softening and working points. A final firing temperature between 900° C. and 1250° C. is desirable to obtain a solid molecular adhesion to the bracket base. Preferably, the fired glaze on the bracket base will have a thickness of 0.001 inch to 0.002 inch.

It is preferred that the liquid glaze be applied to the bracket base by spraying, which includes the steps of fixturing the bracket in an aluminum tray. Next, the brackets are preheated to dry residual moisture off of the bases by preheating at 325° F. for twelve hours. The brackets are then placed on a geared belt set at a belt speed of about 30 inches per minute. The glaze is sprayed on with a Binks spray gun, model No. 115 at 25-26 p.s.i. pressure. The bracket and glaze is then cooled and the brackets with the glaze thereon are transferred to firing trays for the first cycle of glass ceramic glaze sintering process. The "Green" glaze thickness should be about 0.002 inch to 0.004 inch before firing. Upon successful spraying and firing, the glaze will shrink to approximately 50 percent of the initial film thickness, thereby giving its own thickness of 0.001 at 0.002 inch.

The first firing cycle of the glaze using an air fire system includes raising the temperature of the bracket and glaze to 225° C. at a rate of 7° C. per minute in order to burn out the binders. This temperature is held for twenty minutes and then the temperature is ramped up to 1060° C. at 7° per minute. The second temperature is held for sixty minutes, and thereafter the bracket is cooled at the rate of 5° C. per minute to 20° C. This is about room temperature. This assures a solid molecular adhesion of the glaze to the bracket base by eliminating entrapped air in the glaze.

A water-soluble contact adhesive is then applied to the glaze surface. The purpose of accepting a further application of a textured substance which will create a complex surface on the glaze comprised of multi-directional undercuts and projections. While various materials for the textured substance may be used, it has been found that the following exhibit excellent results.

A first composite of textured materials is sharp multi-edged shards of highly purified aluminum oxide with a minimum density of 3.9 grams per cc. The aluminum oxide should be about 99.5% pure. It is important to use a proper mesh size, and the preferred size is 220 mesh. It has been found that larger particle sizes have a tendency to pull out of the fired glaze or fracture the glazed surface when tension is applied. Preferably, the aluminum oxide is of high purity alumina made from the well known Bayer process. The smaller than the 220 mesh size does not provide sufficient mechanical lock or undercut for the dental adhesive. The larger than 220 mesh size also causes the dental composite layer to be too thick, resulting in a weaker bond strength. Also, it has been found that larger shards might break off under tension and fracture the glazed surface.

The contact adhesive is brushed or sprayed onto the bracket bases, after which the 220 mesh aluminum oxide is dusted onto the adhesive surfaces. The excess aluminum oxide is blown off, leaving the alumina grit only on the lingual surface of the bracket base. Preferably, the contact adhesive is of a latex base diluted with thirty percent by volume methanol. For example, it may be the IAC Bond Plus pressure-sensitive adhesive made by Industrial Adhesive Co. of Chicago, Ill., suitably thinned by distilled water or methanol. After application, it is allowed to dry for about one hour prior to being dusted with the textured material.

The electrically fused high purity alumina, a polycrystalline ceramic, made from the Bayer process for the texturing surface is carefully sieved in the proper mesh size for use as it has been determined that particles larger or smaller than the 220 mesh size do not provide a proper mechanical retention or mechanical lock with a dental composite adhesive resin. A suitable adhesive is one of the Bis-GMA bonding composites, such as No-Mix 30 or Force II sold by American Orthodontics Corporation of Sheboygan, Wisc.

A typical composition of the fused alumina is as follows:

| | |
|---|---|
| $Al_2O_3$ | 99.55% |
| $TiO_2$ | .01% |
| $SiO_2$ | .05% |
| CaO | .03% |
| MgO | .02% |
| $Na_2O$ | .14% |

| | |
|---|---|
| -continued | |
| $Fe_2O_3$ | .04% |

A second textured substance that can be used includes the high purity aluminum oxide above referred to in combination with microglass spheres that are chemically inert and which provide small undercuts (mechanical locking) at the point where they embed in the glaze. These spheres are mixed with the aluminum oxide particles above mentioned in an amount of about 25 volume percent. Preferably, again, the spheres are of 220 mesh, the same as the shards of alpha alumina. The spheres are randomly dispersed in the shards. A basic composition of the spheres would be as follows:

| | |
|---|---|
| $SiO_2$ | 93-97% |
| BaO | 1-3% |
| $B_2O_3$ | 3-5% |
| $Na_2O$ | 1-3% |

An ideal composition of the spheres would be as follows:

| | |
|---|---|
| $SiO_2$ | 95% |
| $B_2O_3$ | 4% |
| $N_2O$ | 1% |

Following the application of the textured substance, the bracket is refired to allow the alumina shards or the alumina shards/glass spheres to settle in the molten base. The refiring process includes raising the temperature of the bracket from room temperature to 500° C. at 5° C. per minute rate. When 500° C. is reached, this is held for fifteen minutes to allow a clean burn-off of the contact adhesive. Thereafter, the temperature of the bracket is ramped to 1040° C. at the rate of 7° C. per minute. This temperature is maintained for 240 minutes or four hours. Thereafter, the bracket is cooled at the rate of 5° C. per minute to 20° C. or room temperature. This establishes that chemical and mechanical bonding adheres the texturing material into the glass ceramic glaze so that the bracket/glaze texture material is combined into one entity. The brackets are now ready for final inspection and handling.

A typical twin tie wing ceramic bracket is illustrated in the drawings and generally indicated by the numeral 10. The bracket generally includes a base 11, tie wings 12 and 13, and a horizontally extending and labiobuccally opening archwire slot 14. The base includes a tooth-attaching side 15 onto which is attached a mechanical lock means 20 having a multiplicity of undercuts and projections to coact with an adhesive in bonding the bracket to a tooth. The mechanical lock means 20 will be made and fired to the tooth-attaching side 15, as above mentioned. The lock means 20 is composed of shards of aluminum oxide, while the lock means 20A of FIG. 4 is composed of a mixture of shards and glass spheres/beads.

In view of the foregoing, it will be appreciated that the present invention provides a glass ceramic base and method of making the same for the tooth-attaching side of a ceramic bracket to obtain the mechanical retention ability for use in mechanical adhesives and mechanical bonding so that the brackets may be debonded by exceeding the shear strength of the bonding material without damaging the integrity of the tooth.

It will be understood that modifications and variations may be effected without departing from the scope of the novel concepts of the present invention, but it is understood that this application is to be limited only by the scope of the appended claims.

The invention is hereby claimed as follows:

1. A method of making a mechanical lock means for the tooth-attaching side of a ceramic orthodontic bracket so the bracket may be mechanically bonded to a tooth with a bonding adhesive,
which method comprises the step of preparing a glass frit having a coefficient of thermal expansion slightly lower than that of the bracket, applying the frit to the tooth-attaching side of the bracket, firing the bracket and frit to fuse it to the bracket, applying a water-soluble contact adhesive to the fired frit, preparing a textured substance in the form of aluminum oxide, applying the substance to the adhesive, firing the bracket to allow the substance to settle in the molten glaze, and cooling the bracket.

2. The method of claim 1, wherein the frit is composed of a dry glass-ceramic blend mixed into a liquid comprised of various binders and solvents.

3. The method of claim 2, wherein the various binders and solvents include carbowax, methylcellulose, methanol and de-ionized water.

4. The method of claim 3, wherein the dry glass-ceramic blend includes by weight 60 to 70 percent $SiO_2$, 5 to 13 percent $Al_2O_2$, 8 to 13 percent Ca, 10 to 17 percent Na, and 1 to 5 percent K.

5. The method of claim 3, wherein the dry glass-ceramic blend includes by weight 65 percent $SiO_2$, 9 percent $Al_2O_2$, 10 percent Ca, 14 percent Na, and 2 percent K.

6. The method of claim 3, wherein the frit thickness is about 0.002 to 0.004 inches before firing.

7. The method of claim 6, wherein the frit is applied to the bracket by spraying.

8. The method of claim 7, wherein the bracket is preheated prior to the application of the frit.

9. The method of claim 8, wherein the firing of the bracket and frit includes heating the bracket and frit to about 225° C. and holding that temperature for about twenty minutes, heating the bracket and frit to 1020° C. by raising the temperature about 7° per minute, holding the temperature at 1020° C. for about sixty minutes, and thereafter cooling the bracket and frit to 20° C. at the rate of 5° C. per minute thereby providing a sintered glaze.

10. The method of claim 9, wherein the textured substance comprises sharp multi-edged shards of high purity aluminum oxide having a mesh size of 220 and a minimum density of 3.9 grams per cc.

11. The method of claim 10, wherein the bracket is refired by heating to about 500° C. at the rate of 5° C. per minute, holding the temperature at 500° C. for about 15 minutes, increasing the temperature to about 1040° C. at the rate of 7° C. per minute, holding the temperature at 1040° C. for 240 minutes, and cooling the bracket to 20° C. at the rate of 5° C. per minute.

12. The method of claim 9, wherein the textured substance comprises a mixture of shards of alpha-alumina and randomly dispersed micro-glass spheres having a mesh size of about 220.

13. The method of claim 12, wherein the spheres are 25 percent by volume of the mixture.

14. The method of claim 12 wherein the bracket is refired by heating to about 500° C. at the rate of 5° C. per minute, holding the temperature at 500° C. for about 15 minutes, increasing the temperature to about 1040° C. at the rate of 7° C. per minute, holding the temperature at 1040° C. for 240 minutes, and cooling the bracket to 20° C. at the rate of 5° C. per minute.

15. A mechanical lock means for a ceramic orthodontic bracket made according to the method of claim 1.

16. A polycrystalline ceramic bracket having a mechanical lock on the tooth-attaching side, which mechanical lock comprises a layer of glass ceramic glaze fired to the tooth-attaching side, and a layer of high purity alumina shards fired to the glaze to produce a multiplicity of undercuts and projections capable of coacting with a mechanical bonding material to bond the bracket to a tooth, whereby debonding results from exceeding the bonding strength of the bonding material.

* * * * *